（12） United States Patent
Simola et al.

(10) Patent No.: US 9,422,256 B2
(45) Date of Patent: Aug. 23, 2016

(54) CONTINUOUS PROCESS FOR PRODUCING EPICHLOROHYDRIN FROM GLYCEROL

(71) Applicant: CONSER SPA, Rome (IT)

(72) Inventors: Flavio Simola, Monterotondo (IT); Michele Iosco, Rome (IT)

(73) Assignee: CONSER SPA, Rome (IT)

( * ) Notice: Subject to any disclaimer, the term of this patent is extended or adjusted under 35 U.S.C. 154(b) by 0 days.

(21) Appl. No.: 14/431,881

(22) PCT Filed: Sep. 28, 2012

(86) PCT No.: PCT/IT2012/000300
§ 371 (c)(1),
(2) Date: Mar. 27, 2015

(87) PCT Pub. No.: WO2014/049625
PCT Pub. Date: Apr. 3, 2014

(65) Prior Publication Data
US 2015/0246895 A1 Sep. 3, 2015

(51) Int. Cl.
C07D 301/27 (2006.01)
C07D 301/02 (2006.01)
C07D 303/08 (2006.01)

(52) U.S. Cl.
CPC ............ C07D 301/02 (2013.01); C07D 303/08 (2013.01)

(58) Field of Classification Search
CPC ............................ C07D 301/02; C07D 303/08
USPC ....................................................... 549/514
See application file for complete search history.

(56) References Cited

U.S. PATENT DOCUMENTS

| 2,177,419 | A | 10/1939 | William |
| 449,653 | A | 4/1981 | George |
| 7,982,061 | B2 | 7/2011 | Fan et al. |
| 7,985,867 | B2 | 7/2011 | Fan et al. |
| 2010/0029960 | A1 | 2/2010 | Fan et al. |

FOREIGN PATENT DOCUMENTS

| CN | 102675251 | 9/2012 |
| CZ | 2 937 28 B6 | 7/2004 |
| EP | 0 421 379 A1 | 4/1991 |
| EP | 2 219 779 B1 | 8/2010 |
| GB | 799 567 A | 4/1956 |
| JP | 52000210 | 1/1977 |
| JP | 59196880 | 11/1984 |
| JP | 03145481 | 6/1991 |
| JP | 0788366 | 9/1995 |
| JP | 2009184943 A | 8/2009 |
| JP | 2009263338 A | 11/2009 |
| WO | 2006/020234 A1 | 2/2006 |
| WO | 2008/101866 A2 | 8/2008 |
| WO | 2008/152043 A1 | 12/2008 |
| WO | 2010/014892 A2 | 2/2010 |
| WO | 2010/014898 A2 | 2/2010 |
| WO | 2011/092270 A2 | 8/2011 |

OTHER PUBLICATIONS

International Search Report, dated Jan. 4, 2013, from corresponding PCT application.

*Primary Examiner* — T. Victor Oh
(74) *Attorney, Agent, or Firm* — Young & Thompson

(57) ABSTRACT

A process for the continuous production, through the glycerine route, of epichlorohydrin from dichlorohydrins, in the presence of an alkali solution, wherein the reactive column for the reaction of dichlorohydrin to epichlorohydrin is characterized by single or multiple feed injections and by multiple alkali solution injections, in order to optimize the epichlorohydrin production and to minimize the aqueous effluents in quantity and in organic contaminants.

20 Claims, 3 Drawing Sheets

CONTINUOUS PROCESS FOR PRODUCING EPICHLOROHYDRIN FROM GLYCEROL

The present invention relates to a process for the continuous production, through the glycerine route, of epichlorohydrin from dichlorohydrins, in presence of an alkali solution, wherein the reactive column for the reaction of dichlorohydrin to epichlorohydrin is characterized by single or multiple feed injections and by multiple alkali solution injections, in order to optimize the epichlorohydrin production and to minimize the aqueous effluents in quantity and in organic contaminants.

BACKGROUND OF THE INVENTION

The present invention relates to a process for the continuous production of epichlorohydrin (ECH) from dichlorohydrins (DCH), with the 1,3 type prevailing over the 1,2 type, in presence of an alkali solution, wherein the DCH's are produced by a continuous catalyzed process using raw or purified glycerol and hydrogen chloride as feedstocks.

Epichlorohydrin is produced by dehydrochlorination of the DCH by means of an aqueous solution of alkali.

Despite there are different processes for the production of epichlorohydrin, such as the conventional process via allyl chloride starting from propylene and chlorine, the Showa Denko process using allyl acetate as reaction intermediate, and the process starting from glycerol and hydrogen chloride, also called GTE (glycerol to epichlorohydrin), brought to the industrial stage only recently, but having its technological principles well known since more than one century, the dehydrochlorination process in all these processes has been subject to limited improvements.

The principles of this process is to allow a dehydrochlorination reaction, in which the dichlorohydrins (1,3 or 1,2) are converted to epichlorohydrin in presence of an alkali, with the formation of water and of the corresponding chloride salt, as explained in the reaction scheme below:

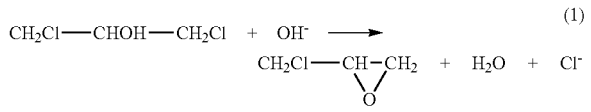

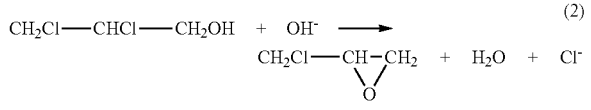

The rate of conversion is high, somewhat more rapid for the 1,3 isomer in comparison with the 1,2 isomer, and it is generally favored by increasing the temperature or the alkalinity.

The yields of the dehydrochlorination reactions (1) and (2) above are limited by the presence of side reactions.

The main side reaction is the hydrolysis of the ECH to monochlorohydrin (3), glycidol (4) or glycerol (5):

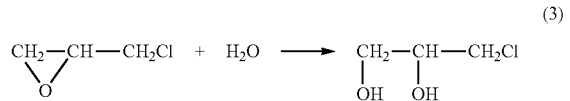

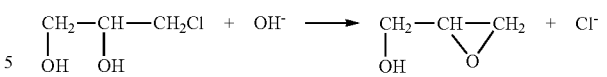

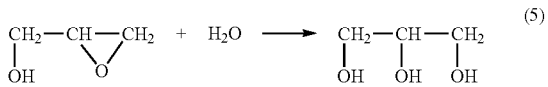

The hydrolysis of epichlorohydrin is catalyzed by alkali or acids, but it takes place, even if at a lower rate, also at neutral conditions.

Direct condensation of epichlorohydrin, favored by alkaline conditions, can lead to the formation of poly-glycols. Some chloroethers may be formed by the reaction of a dichlorohydrin with epichlorohydrin.

Since all the side reactions occur in the liquid phase, the best method to increase the overall yields is to strip-out the epichlorohydrin as soon as it is formed, feeding the crude dichloropropanol, after mixing with alkali, in counter-current flow of steam in a reactive distillation type column.

Moreover, it is well known since more than 40 years by the engineers and operators skilled in the dehydrochlorination problems that a residence time not higher than 20 seconds, and even better not higher than 10 second, shall be used in the reaction trays to avoid the degradation of epichlorohydrin.

As regard the operating conditions commonly used for this reactive distillation column, it usually works at a pressure slightly higher than atmospheric, and at temperatures between 100 and 120° C. (temperature at the column bottom).

The heat to the column is usually provided using live steam, with or without a vapor thermocompression of the bottom product of the column, consisting in salted water, which is depressurized and partially vaporized under slight vacuum conditions.

The heavy by-products formed in the reactive column, as glycidol, glycerol and poly-glycerol, are not stripped by the live steam and, therefore, they are lost in the aqueous bottom stream together with the salts. As a consequence, the inefficiency in the reaction impacts also in the quality of the waste water subject to a treatment, before to be disposed or recycled.

Alkali type and activity also affect the reaction yields; the more common calcium hydroxide $Ca(OH)_2$, as freshly prepared and homogenous water slurry, is used or, as a different option, caustic soda, as NaOH diluted solution, can also be used.

The major difference in the operating conditions of this column between the conventional process (from chlorine and propylene) and the process of the present invention (from glycerol and hydrogen chloride), is the different concentration in DCH of the feedstock. In fact, while in the conventional technology a very diluted stream of DCH's in water (around 3-4% wt) is fed to the dehydrochlorination, in the process according to the invention, the DCH's are produced in a very high concentration (usually more than 95% wt). This feature of the new process allows to produce a much lower amount of water effluent from the bottom of the dehydrochlorination column, but, on the other side, it requires the use of caustic soda instead of milk of lime slurry, due to the severe trays fouling and the operating problems which can occur. Unfortunately the use of caustic can be the cause of further problems because, owing to its reactivity higher than milk of lime, it may produce an higher quantity of by-products due to the faster re-conversion of the produced ECH to glycidol or glycerol.

Another important difference of the process from glycerol according to the invention is the nature of the dichlorohydrins. While in the conventional process the reaction between allyl chloride and hypochlorous acid produces mainly the 1,2 DCH compound, in the new process the catalytic reaction of glycerol with hydrogen chloride produces 1,3 DCH with a selectivity higher than 90%. It is known from the technical literature than the 1,3 dichlorohydrin is much more reactive than the 1,2 DCH, because the intermediate ion bringing to the formation of epichlorohydrin of the 1,2 compound is less stable.

A third point of distinction of the process from glycerol according to the invention, is connected to the production of water in the hydrochlorination reaction of the glycerol with hydrogen chloride and the consequent advisability to remove at least part of the reaction water to favor the reaction kinetic and conversion. The removal of water by evaporation is necessarily joined by a partial vaporization of hydrogen chloride, which has to be neutralized or recovered as hydrochloric acid solution, and of dichlorohydrins which shall be recovered through their conversion to epichlorohydrin.

In conclusion the higher reactivity of both the reactants of the process of the present invention, the 1,3 DCH and the sodium hydroxide, compared to the 1,2 DCH and the calcium hydroxide respectively mostly present in the conventional process, together with the much higher concentration of the dichlorohydrin stream and to the possible presence of a second vapor feed, suggest the use of a different arrangement and different operating conditions of the reactive system to produce epichlorohydrin.

Different patents have been published related in general to the process of producing ECH, and some particularly related to possible solution of one or more of the problems listed above. Here below are reported the most significant.

U.S. Pat. No. 2,177,419 published on Oct. 24, 1939 may be considered among the first applications considering the reaction of the dichlorohydrin, produced from allyl chloride, with an excess of basic metal hydroxide, particularly with an aqueous slurry of calcium hydroxide, and the following stripping of epichlorohydrin with live steam at atmospheric pressure. The patent also remarks the importance of the low residence time in the reactor. Among other things, it quotes as follows: if the contact time of the epihalohydrin with the alkaline reaction mixture is made negligible at the temperature of separation of the former therefrom, higher separation temperatures may be used without substantial destruction of the epihalohydrin.

British patent GB 799,567 and European patent EP 0421379 try to solve this problem using a solvent extraction (trichloropropane or glycol-ether respectively), to separate the produced epichlorohydrin from the aqueous phase.

The Japanese patent JP 52000210 relates to a saponification column using perforated trays without liquid downcomers to minimize the residence time, and another Japanese patent JP 59196880 describes a saponification column with combined feed of milk of lime and caustic soda solution, to avoid loss of product in the column bottom.

U.S. Pat. No. 4,496,53 relates to a double step saponification process, made by a back-mix reactor and a plug-flow reactor, both in presence of an inert organic solvent, as carbon tetrachloride.

The Japanese application JP 3145481 solves the problem of unconverted DCH loss in the top of the column, by using, before the total condenser, a partial condenser to recover, by refluxing them to the column, the DCH lost in the top with the product.

The subject of the Japanese patent JP 63017874 is a saponification column, where DCH and milk of lime are not premixed before entering in the column, but where the milk of lime feed is fed separately at a higher position respect to the DCH feed.

The Czech application CZ 293728 describes a saponification column designed in a way that the tray liquid load, in order to minimize the residence time, is the minimum possible to maintain hydraulic stability.

More recent patent applications related to the saponification column in a epichlorohydrin from glycerol process are between the others: WO 2011/092270, where membranes are used in the saponification column to separate the two phases of the distillate, JP 2009/263338, where the ratio 1,3/1,2 DCH is fixed to control the properties of the organic and the aqueous phases in the saponification distillate, and JP 2009/184943, where, instead of a reactive column, a CSTR type reactor is used with a simultaneous distillation of the produced epichlorohydrin.

Other patents from Solvay S.A. relate to the dehydrochlorination step of the process to produce epichlorohydrin from glycerol. The invention of EP 2132190 and EP 2160356 describes a process for producing epichlorohydrin, wherein the glycerol dichlorohydrin reacts with a basic compound and the product of reaction is subjected to a decantation process, where one fraction contains most of the epichlorohydrin produced and a second aqueous fraction contains most of the salt produced in the reaction. Substantially it represents a method rather different from the conventional reactive column.

Other three patents by Dow Global Technologies US 2010/0029960, U.S. Pat. No. 7,982,061 and U.S. Pat. No. 7,985,867 relate to a process and apparatus for the dehydrochlorination of dichlorohydrins with production of epichlorohydrin. The first, more specifically, refers to the mixing of the dichlorohydrin stream with a base water solution in a plug flow mixer-reactor, the second to the operating conditions of the reflux drum to be used to minimize the hydrolysis losses, the third wherein the inventive step lies in maintaining the liquid holdup per tray below certain values of residence time, depending from the section of the column (top, feed and bottom zones). Each of the three patents refers to a particular feature able to reduce the hydrolysis reactions with by-products formation. All the examples included in these patents refer to a stream of dichlorohydrins produced by glycerol chlorohydrination.

As shown in the above patents description, during the years have been done some efforts to solve separately the problems related to the saponification reaction, but none of the patents is related, in a complete and organic way, to the dehydrochlorination column for solving the different problems and, at the same time, this problem has not yet been considered taking into account the new features of the processes for production of epichlorohydrin from glycerol. The scope of this patent is to propose a dedicated process for the dehydrochlorination, that allows to improve the performances of the column in terms of higher yields in epichlorohydrin and better quality of the waste water produced at the column bottom.

SUMMARY OF THE INVENTION

The present invention relates to a process for the continuous production of epichlorohydrin (EPI) from dichlorohydrins (DCH), with the 1,3 type prevailing over the 1,2 type, in presence of caustic soda solution, wherein the DCH's are produced by a continuous catalyzed process using raw or purified glycerol and hydrogen chloride as feedstocks.

The process from glycerine, by a comparison with the conventional process via allyl chloride, shows at the same time three different factors which separately contribute to increasing the rate of reaction of the DCH's to epichlorohydrin, but which also promote the hydrolysis reaction, bringing to the production of undesired amount of glycerol and other by-products, as follows:
   a. the much higher concentration of the DCH (in the conventional process the DCH are diluted in a huge amount of water)
   b. the use of caustic soda (water solution) rather than milk of lime (water slurry). In fact the reaction rate is proportional to the OH⁻ ions concentration; actually, if $Ca(OH)_2$ is employed as reagent, due to its limited solubility in water, the OH⁻ concentration does not change significantly as the reaction proceeds, because a buffered solution $Ca(OH)_2$—$CaCl_2$ is formed. According to the technical literature (Industrial Engineering Chemistry Process Des. Dev., Vol. 18, No. 3, 1979), during the reaction of DCH with calcium hydroxide, the concentration of hydroxyl ions decreases very slowly after the initial stage of reaction. On the contrary by employing caustic soda, it is practically fully decomposed and, therefore, the concentration of the hydroxyl ions at the point of mixing with the dichlorohydrin is very high.
   c. contrary to the conventional process, the 1,3 dichlorohydrin, which is much more reactive than the 1,2 DCH, is the prevailing form.

In conclusion the combined action of the factors described in the above point a, b and c causes, if the reaction is produced in the same apparatus and using the same operating parameters of the conventional process, an abnormal formation of undesired by-products.

Therefore the present invention provides a desired process for the production of epichlorohydrin from dichlorohydrins deriving from the hydrochlorination of glycerol with hydrogen chloride, overcoming the problems of the known processes.

One aspect of the invention is a process of dehydrochlorination for the continuous production of epichlorohydrin by the reaction of concentrated dichlorohydrin, where the 1,3 is prevailing, with a slight excess of caustic soda solution in a reactive column, wherein said process comprises:
   1. contacting all the concentrated dichlorohydrin stream with only a fraction of the caustic soda solution, in amount lower than the stoichiometric value, in a mixing device, preferably of the static mixer type. It was found that the best results are reached if the amount of caustic soda joining the dichloroydrin feed in the external mixer is at least 80% but not higher than 95% of the stoichiometric value to convert the dichloroydrin to epichlorohydrin and to neutralize, is any, the hydrogen chloride in the feed to sodium chloride
   2. feeding the combined stream from the mixer to a reactive distillation column, including, below the feed point, few trays with low liquid residence time, preferably of the segmental type or disc and doughnut type without downcomers, followed by other few trays at higher efficiency, preferably of valve or sieve type.
   3. feeding the remaining part of the caustic soda solution distributed in one to three different trays below the high efficiency trays, in order to keep about constant at the points of injection along the column the mass ratio between the caustic soda and the dichlorohydrin.
   4. using, in the above section with caustic injection, trays with low liquid residence time, preferably of the segmental type or disc and doughnut type without downcomers.
   5. using in the bottom section of the column, where almost all dichlorohydrin is reacted, trays at high efficiency, preferably of valve or sieve type.
   6. vaporizing part of the aqueous product from the column bottom in a bottom reboiler using steam at low pressure, without direct use of live steam injected at the column bottom.
   7. stripping the epichlorohydrin in the column as soon it is formed, condensing the mixture of epichlorohydrin, water and small amount of light by-products from the column overhead in a condenser using cooling water or air, separating the resulting two liquid phases and refluxing to the column top section the aqueous phase, containing epichlorohydrin with concentration equal or slightly higher of its solubility in water at the condensing temperature.

The core aspect of the present invention is the distribution of the caustic soda in different points of the system, in order to maintain it as much as possible in stoichiometric defect with respect to the dichlorohydrins. Nevertheless, since a not enough amount of caustic soda could produce also an unsatisfactory conversion of the dichlorohydrin, a final part of the caustic solution, such as to bring again its amount in excess respect the DCH, is added in an intermediate section of the reactive column, where most of the epichlorohydrin, which is lighter than the dichlorohydrins, has been already stripped out by the countercurrent stream of steam.

It has been found that the best result in terms of by-products reduction are reached if the total amount of caustic soda sent to external mixer, plus the amount sent to the multiple feed injection of the column, is at least 101% but not more than 110% of the stoicvalue to convert the dichloroydrin to epichloroydrin and to neutralize, if any, the hydrogen chloride in the feed to sodium chloride.

The operating pressure of the column is in a range between 200 mbar absolute and 1.5 bar absolute, preferably it shall be below the atmospheric pressure, at a value between 400 mbar and 800 mbar.

The choice to operate under a slight vacuum allows: (i) a reduced hydrolysis of the product to glycerol, (ii) an easier stripping of the epichlorohydrin produced, and (iii) an higher reboiler differential temperature, with consequent reduced capital cost and use of steam at lower pressure.

The operating temperature of the column bottom is selected between 75 and 110° C., preferably between 85 and 99° C.

Within the scope of this invention, also the column internals have to be selected to maximize the yield to epichlorohydrin: the top section, above the main feed, is made by packing, random or structured, with the scope of partially recover the dichlorohydrins not reacted in the trays below and of re-vaporize the epichlorohydrin contained in the aqueous reflux.

The middle section, following the arrangement of the different injections of feed and caustic soda solution, is characterized by a succession of baffle trays, designed to allow epoxidation reaction of DCH minimizing residence time, and valve or sieve trays, designed to efficiently strip-out the produced epichlorohydrin.

The lower section is characterized by valve trays designed with a standard liquid residence time, allowing the conversion of residual heavy chlorinated by-products to glycerol, that is more easily treated in the waste water disposal system.

A further improvement in the column has been introduced by the use of a shell and tube heat exchanger as reboiler instead of the more commonly used live steam: this feature, as explained above, is possible thanks to the low operating pressure of the column; such indirect use of steam allows a much lower quantity of water in the bottom effluent of the column. This feature, together with the inherent advantage of the GTE process, that produces very concentrated DCH with a very low quantity of water, represents a big advantage as environmental impact: the resulting waste water amount is about ten times less than in the conventional process.

The use of the reboiler, together with the mentioned high DCH's concentration in the feed and with the use of caustic soda solution at a sodium hydroxide concentration not lower than 10 wt % or, preferably, not lower than 15 wt % or even more preferably between 18 to 25 wt %, allows the production at the bottom of the column of an aqueous stream with rather high concentration of sodium chloride, at least higher than 15 wt %, or preferably at least 20 wt % but in any case below the solubility limit of the salt, around 27.5 to 28 wt % at the temperature of the column, to avoid any undesired precipitation and accumulation of solid salts in the column trays. The production of an aqueous effluent with high concentration in sodium chloride permits, unlike the conventional process via allyl chloride, to reuse this stream, after an adequate treatment to reduce its organic content, normally according to this invention between 500 to 1000 mg/l expressed as total organic carbon (TOC), to an electrolytic process for the production of chlorine and sodium hydroxide solution.

Another peculiarity of the dehydrochlorination column applied to the process from glycerine is the possibility of a multiple dichlorohydrin feed system. With reference, for instance, to the European patent EP 2219779 assigned to Conser S.p.A., the proposed process includes a partial vaporization of the effluent from both stages of reaction and the feeding of such vapor streams to the dehydrochlorination column (see also claims 2 and 3 and FIG. 1).

While the main liquid stream to the dehydrochlorination is usually very rich in DCH, the vapour stream is normally a mixture of water, hydrogen chloride, DCH and traces of MCH, being the content of water substantially higher than 50% and the content of HCl higher than 10%.

Ideally the vapor stream should be sent directly to an intermediate section of the dehydrochlorination column, in order to both recover the DCH, which can be converted to epichlorohydrin, and use its vapor water content as a way contributing to evaporate the epichlorohydrin, reducing in this way the consumption of steam in the bottom reboiler. Unfortunately, due to its high content of acid, the direct use of such stream may cause severe localized corrosion of the dehydrochlorination column at its inlet point, before the HCl is neutralized by the caustic soda.

On the other hand the condensation and following neutralization with a base of this stream should cause the waste of its thermal energy, by losing the possible reduction of steam consumption at the reboiler.

We have found a solution how to avoid the corrosion of the column, without losing its energy content.

In another embodiment of the present invention, whenever this gaseous stream is present, it is subject to a first neutralization in a static mixer by means of a diluted caustic soda solution injection to produce, by an adiabatic operation, a two phases mixture, which is split in a liquid/vapor separator. The obtained liquid, rich in water, DCH and neutralization salt, and vapour feeds, rich in DCH and water, are directly fed to the dehydrochlorination column.

These three different feed streams, the main liquid feed from the static mixer, and the vapor and liquid feed from the neutralization/partial condensation, are fed to the column at different trays, depending from their composition: the highest one is the liquid stream rich in DCH that, after a first premixing with a caustic soda solution, is injected in the column almost in the top section, to minimize the residence time of the produced ECH in the column after the reaction; the other two feed streams are positioned along the column according to their composition: higher is the DCH concentration, more the feed position will be high; on the contrary, higher is the content of salt, water and MCH, that cannot be converted to ECH, more the inlet position will be low.

In this second aspect, the invention relates to a process of dehydrochlorination for the continuous production of epichlorohydrin in a reactive column wherein, besides a main liquid feed with high concentration of 1,3 dichlorohydrin, another secondary vapor feed is present, containing water at more than 50 wt %, hydrogen chloride, DCH and MCH, wherein the process comprises:

1. contacting the concentrated dichlorohydrin stream with only a fraction of the caustic soda solution, in amount lower than the stoichiometric value, in a mixing device, preferably of the static mixer type. It was found that the best results are reached if the amount of caustic soda joining the dichloroydrin fees in the external mixer is at least 80% but not higher than 95% of the stoichiometric value to convert the dichloroydrin to epichlorohydrin and to neutralize, is any, the hydrogen chloride in the feed to sodium chloride
2. feeding the combined stream from the mixer to a reactive distillation column, including, below the feed point, few trays with low liquid residence time, preferably of the segmental type or disc and doughnut type without downcomers, followed by other few trays at higher efficiency, preferably of valve or sieve type.
3. contacting the vapor feed containing water, hydrogen chloride, dichlorohydrins and monochlorohydrins with a second stream of diluted caustic soda, in amount corresponding to the neutralization of its acid content, in a second mixing device, preferably of the static type. The amount of caustic soda joining the dichloroydrin feed in the external mixer is at least 110% of the stoichiometric value to neutralize to sodium chloride the hydrogen chloride contained in the vapor feed.
4. separating the vapor and liquid phases from the second static mixer and feeding them to two different trays of the reactive column.
5. feeding the remaining part of the caustic soda solution distributed in two to four different trays below the secondary feed section, in order to keep about constant at the points of injection along the column the mass ratio between the caustic soda and the dichlorohydrin.
6. using, in the above section with caustic injection, trays with low liquid residence time, preferably of the segmental type or disc and doughnut type without downcomers.
7. using in the bottom section of the column, where almost all dichlorohydrin is reacted, trays at high efficiency, preferably of valve or sieve type, minimizing the content of chlorinated organic in the bottom aqueous product.
8. vaporizing part of the aqueous product from the column bottom in a bottom reboiler using steam at low pressure, without direct use of live steam injected at the column bottom.
9. stripping the epichlorohydrin in the column as soon it is formed, condensing the mixture of epichlorohydrin, water and small amount of light by-products from the column overhead in a condenser using cooling water or air, separating the resulting two liquid phases and refluxing to the column top section the aqueous phase, containing epichlorohydrin with concentration equal or slightly higher of its solubility in water at the condensing temperature.

It has been found that the best results in terms of by-product reduction are reached if the total amount of caustic soda sent to the external mixers, plus the amount sent to the multiple feed injection of the column is at least 101% but not more than 110% of the stoichiometric value, to convert the dichloroydrin to epichloroydrin and to neutralize, if any, the hydrogen chloride in the feeds to sodium chloride.

The following figures explain in detail the peculiar arrangement of the column and of its ancillaries, as described in the paragraphs above.

DETAILED DESCRIPTION OF THE INVENTION

Figure 1:
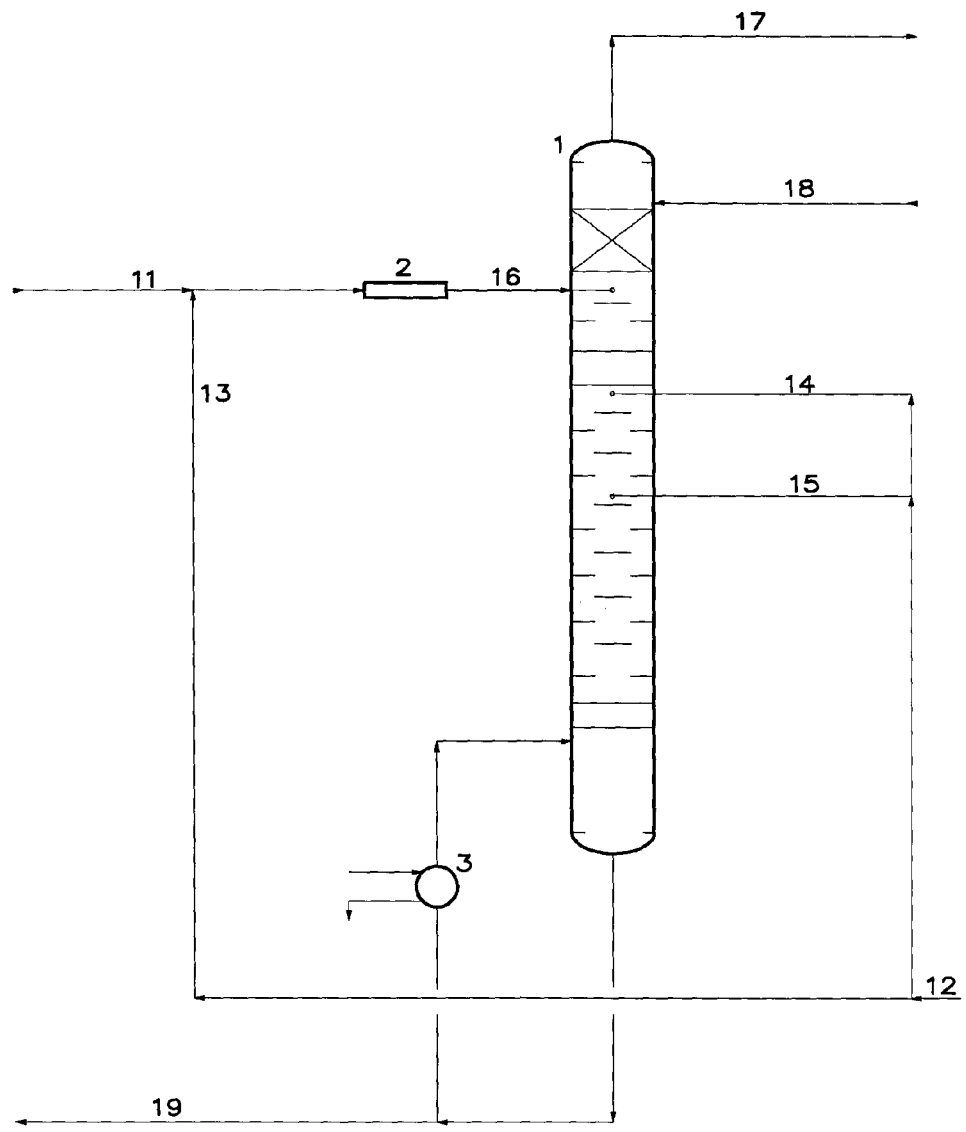
FIG. 1 is a simplified process flow diagrams of the reactive column for the dehydrochlorination of a stream rich of dichlorohydrins produced from glycerine and hydrogen chloride, as described for one aspect of the invention in the summary of the disclosure points 1 to 7.

A schematic diagram of the dehydrochlorination reactive column is shown in FIG. 1.

The liquid stream 11, rich in dichlorohydrins (more than 90% wt), represents the main feedstock to the reactive column 1. It is first premixed with a caustic soda aqueous solution, stream 13, in a static mixer 2; its amount is slightly below the stoichiometric value, in order to minimize the degradation reaction of epichlorohydrin. The dehydrochlorination reaction, sometime also called saponification, is very fast and the epichlorohydrin just formed, stream 16, as soon as it enters the column 1, is immediately stripped in the first baffle trays and then in the valve trays under the feed section. A fraction of not reacted dichlorohydrins in the vapour phase is recovered in the top packing section, by washing with the aqueous column reflux 18.

The top product of the column 17 consists of the produced epichlorohydrin, water above its azeotropic composition with epichlorohydrin, and still some minor amount of not converted dichlorohydrins and of light impurities, which are sent to a condensation and phase separation system. The resulting aqueous phase 18, containing epichlorohydrin and dichlorohydrins at their solubility in water at the condensing temperature, is refluxed back to the top of the column 1.

To keep constant the ratio between DCH and caustic soda, the total quantity of caustic soda solution 12 fed to the column is split in the main stream 13, which joins the main feedstock 1, and in two side injections along the column, streams 14 and 15. The flowrates of stream 14 is controlled in way to avoid caustic soda excess along column trays, minimizing the by-products formation, and maximizing the epichlorohydrin production. Only by the injection of stream 15 the overall amount of caustic soda slightly exceeds the stoichiometric amount, without anyway being detrimental for the yields of reaction, since the amount of epichlorohydrin still present in the tray of injection of stream 15 is negligible.

The bottom part of the column 1 is characterized by valve trays and by a long residence time, to allow final conversion of residual chlorinated by-products to glycerol, that is more easily treatable.

The major quantity of water is obtained as bottom product 19 from column 1, together with salt (mostly sodium chloride), and organic by-product (mostly glycerol). To minimize the quantity of water present in the column, an external heat exchanger 3 is used instead of live steam as vaporizing medium.

Figure 2:
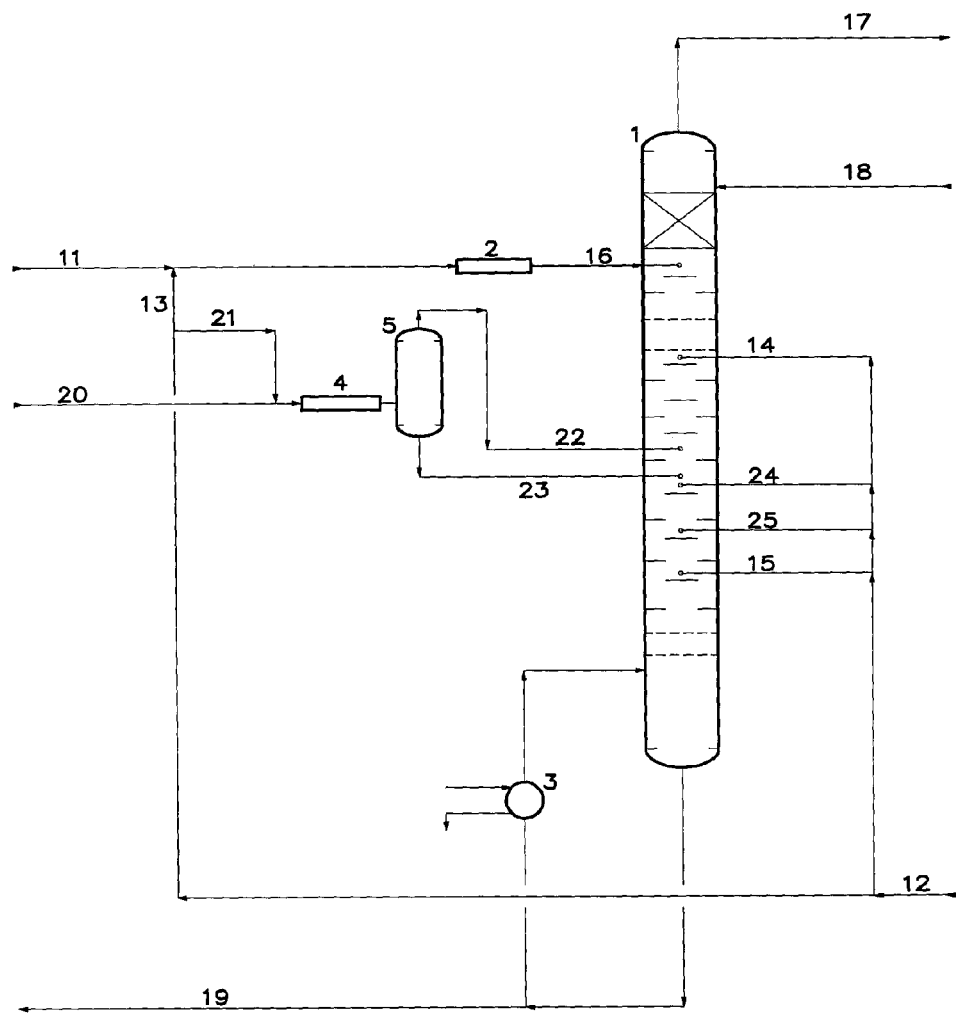
FIG. 2 is a simplified process flow diagrams of the reactive column for the dehydrochlorination of dichlorohydrins produced from glycerine and hydrogen chloride, as described in the summary of the disclosure points 1 to 9 for a second aspect of the invention wherein, besides a main liquid feed with high concentration of 1,3 dichlorohydrin, there is another secondary vapor feed containing more than 50% of water, hydrogen chloride, DCH and MCH.

FIG. 2 shows a schematic diagram of the dehydrochlorination reactive column, wherein, beside the main liquid feed with dichlorohydrins at high concentration, a second vapor stream, in which the main component is water but including also hydrogen chloride, dichlorohydrin and small amount of monochlorohydrin, is fed to the reactive column.

The liquid stream 11, rich in dichlorohydrins (more than 90% wt), represents the main feedstock to the reactive column 1. It is first premixed with a caustic soda aqueous solution, stream 13, in a static mixer 2; its amount is slightly below the stoichiometric value, in order to minimize the degradation reaction of epichlorohydrin. The dehydrochlorination reaction is very fast and the epichlorohydrin just formed, stream 16, as soon as it enters the column 1, is immediately stripped in the first baffle trays and then in the valve trays under the feed section. A fraction of not reacted dichlorohydrins in the vapour phase is recovered in the top packing section, by washing with the aqueous column reflux 18. The top product of the column 17 is composed by the produced epichlorohydrin, water above its azeotropic composition with epichlorohydrin, and still some minor amount of not converted dichlorohydrins and of light impurities, which are sent to a condensation and phase separation system. The resulting aqueous phase 18, containing epichlorohydrin and dichlorohydrins at their solubility in water at the condensing temperature, is refluxed back to the top of the column 1.

The vapour stream 20, containing mostly water, dichlorohydrins, hydrogen chloride and some traces of monochlorohydrin, represents a second possible feed to the column. It comes from the reaction section of the glycerine with hydrogen chloride and it represents the fraction of the reactors effluent which has been vaporized or after a first stage of reaction to reduce its water content or after the final stage of reaction to reduce its content in water and hydrogen chloride, before the distillation under vacuum conditions of the dichlorohydrins. The stream 20, due to its acid content, before entering the reactive column made of materials of construction not suitable for high acidity, needs to be neutralized. The acids contained in this vapor stream are neutralized in the static mixer 4 by means of an injection of caustic soda solution 21. The amount of the neutralizing soda 21 is controlled in order to be in stoichiometric excess respect the amount needed to neutralize the hydrogen chloride contained in the stream 20, but below the stoichiometric value to convert the dichlorohydrins to epichlorohydrin. By operating in such way, any possible corrosion phenomena in the reactive column is avoided and, at the same time, the further conversion of epichlorohydrin to glycerine is minimized. The resultant two phases from the static mixer 4 are separated in the apparatus 5, with the vapour phase 22 rich in epichlorohydrin, DCH and water, and the liquid phase 23, rich in DCH, water and sodium chloride salt.

Due to their different concentration in DCH, the injection points of these streams to the reactive column are different and lower respect to stream 16. Other baffle trays are provided in this section to minimize the liquid residence time To balance this multiple injection of feeds along the column 1 and to keep constant the ratio between DCH and caustic soda, the total quantity of caustic soda solution 12 fed to the column is split in the main stream 13, which joins the main feedstock 1, and in side injections along the column, streams 14, 15, 21, 24 and 25. The flowrates of these streams are controlled in way to avoid caustic soda excess along column trays, minimizing the by-products formation and maximizing the epichlorohydrin production. Only by the injection of the lowest stream 15, the overall amount of caustic soda slightly exceeds the stoichiometric amount, without anyway being detrimental for the yields of reaction, since the amount of epichlorohydrin still present in the tray of injection of stream 15 is negligible.

The bottom part of the column 1 is characterized by valve trays and by a long residence time, to allow final conversion of residual chlorinated by-products to glycerol, that is more easily treatable.

The major quantity of water is obtained as bottom product 19 from column 1, together with salt (mostly sodium chloride), and organic by-product (mostly glycerol). To minimize the quantity of waste water produced by the column, an external heat exchanger 3 is used as vaporizing medium, rather than live steam as traditionally used in the conventional process via allyl chloride.

Figure 3:
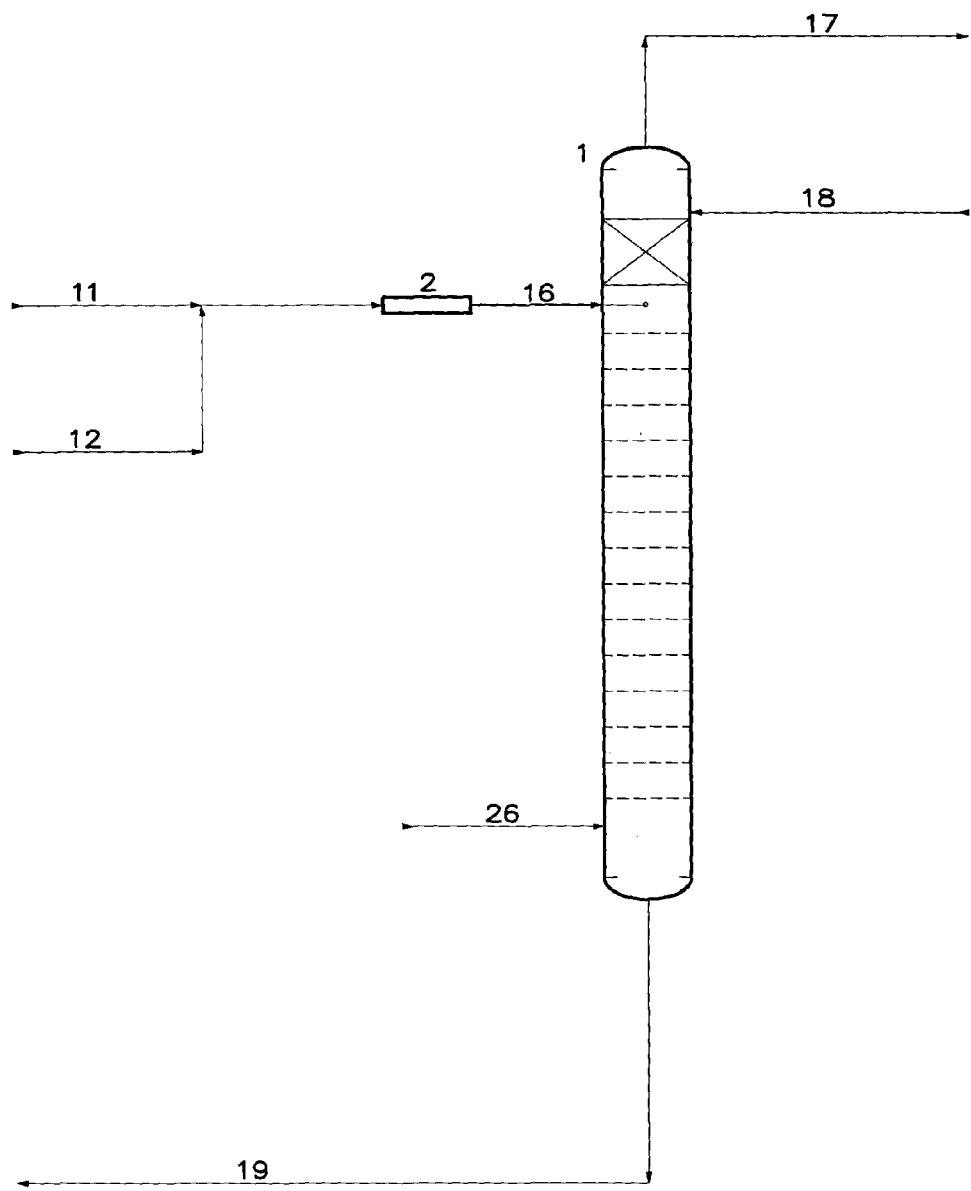
FIG. 3 represents a simplified flow diagram of the reactive column for the dehydrochlorination of a stream containing dichlorohydrin, according to the conventional arrangement with all the alkali solution joining the dichlorohydrin feed.

FIG. 3 shows a schematic diagram of the dehydrochlorination reactive column, according to a conventional process wherein a single alkali solution is used.

The liquid stream 11, rich in dichlorohydrins, represents the main feedstock to the reactive column 1. It is first premixed with a caustic soda aqueous solution, stream 12, in a static mixer 2; its amount is above the stoichiometric value. The dehydrochlorination reaction is very fast and the epichlorohydrin just formed, stream 16, as soon as it enter the column 1, is immediately stripped in the trays under the feed. A fraction of not reacted dichlorohydrins in the vapour phase is recovered in the top packing section, by washing with the aqueous column reflux 18. The top product of the column 1 is composed by the produced epichlorohydrin, water above its azeotropic composition with epichlorohydrin, and still some minor amount of not converted dichlorohydrins and of light impurities, which are sent to a condensation and phase separation system. The resulting aqueous phase 18, containing epichlorohydrin and dichlorohydrins at their solubility in water at the condensing temperature, is refluxed back to the top of the column 1. The major quantity of water is obtained as bottom product 19 from column 1, together with salt (mostly sodium chloride), and organic by-product (mostly glycerol). Live steam injected at the column bottom is used as vaporizing medium.

EXAMPLES

In a 50,000 MT/Y epichlorohydrin manufacturing plant from glycerin and hydrogen chloride, a stream of around 9 t/h of purified dichlorohydrins, containing 85.5 wt % of 1,3 DCH, around 5.5% of 1,2 DCH, around 8.5% of water and small amount of organic impurities, is the main feed of a dehydrochlorination reactive column, where, by the addition of a solution of caustic soda, they are transformed to epichlorohydrin, with parallel production of sodium chloride and water.

A secondary vapor feed with flowrate of around 3.5 T/h, containing around 60 wt % of water, 18% of hydrogen chloride, 20% of dichlorohydrin and other amounts of monochlorohydrin and organic impurities, is produced by partial evaporation of the hydrochlorination reactor effluent.

The following examples, relevant to demonstrate the advantages of the present invention, are the result of computer simulations, using a kinetic and thermodynamic model set up through experimental tests and operating data in industrial plants. The main feed joins a stream of sodium hydroxide solution at 19 wt % concentration. The condition of operation are 300 mm Hg and 72° C. at the overhead, and 500 mm Hg and 93° C. at the bottom. The reactive column contains 16 trays, 4 above the liquid feed inlet and 12 below.

The heat source is low pressure steam fed to a bottom recirculation reboiler. The overhead vapors, a mixture of epichlorohydrin and water with minor amount of unreacted dichlorohydrins and other organic impurities, are condensed by cooling water or air and the resulting two liquid phases are separated in a decanting vessel: the organic phase, containing more than 1 wt % of soluble water is the crude epichlorohydrin, with content higher than 95%, sent to the purification section, while the aqueous phase, containing more than 6% of soluble epichlorohydrin, is refluxed back to the dehydrochlorination column.

Comparative Examples 1 to 3

The following examples 1 to 3 relate to a conventional arrangement of the dehydrochlorination column. The secondary vapor feed is condensed in a dedicated heat exchanger by using of cooling water and joins the main liquid feed. All the caustic soda aqueous solution at 19% concentration, in excess to the chemical consumption for the production of epichlorohydrin and the neutralization of the entering hydrogen chloride, joins the liquid feed in a static mixer before entering the reactive column.

The column performances have been checked for two different reboiler duties, as shown for example 1 and 2 in table 1. In both cases the excess of caustic is 5%.

The example 3 represents the same conditions of example 1, by reducing the caustic excess from 5% to 2%.

TABLE 1

| Example | Caustic excess % | Heat duty KW | Steam/ECH ratio Kg/Kg | Column reflux ratio Kg/Kg |
|---|---|---|---|---|
| 1 | 5 | 7100 | 1.85 | 1.4 |
| 2 | 5 | 8950 | 2.35 | 1.8 |
| 3 | 2 | 7100 | 1.85 | 1.4 |

The attached table 2 shows the most representative results in the three mentioned examples.

In example 1 the Total Organic Carbon of the aqueous bottom product is 1258 mg/l.

Example 2 shows that an increased amount of heat supplied to the reboiler and the subsequent increase of the reflux ratio are not sufficient to produce a significant reduction in term of TOC content of the bottom aqueous stream. It also means that a big portion of the hydrolysis reactions occurs in the static mixer, where the epichlorohydrin produced is still in liquid phase, rather than in the fractionation/reaction trays, where most of the epichlorohydrin is vaporized by contact with a countercurrent stream of steam.

Example 3 shows that, by reducing the excess of caustic soda, the hydrolysis reactions may be slightly restrained. Further reduction of the excess below 2% is difficult to achieve, since it can originate a not complete conversion of the dichlorohydrins in the column, which, besides to represent a loss of product, may increase the TOC of the aqueous waste and, more in particular, its content in chlorinated organic.

TABLE 2

| Example | ECH yield % | Glycerol at bottom wt % | Residue TOC mg/l |
|---|---|---|---|
| 1 | 98.9 | 0.29 | 1258 |
| 2 | 98.9 | 0.28 | 1238 |
| 3 | 98.9 | 0.25 | 1109 |

Example 4

According to the Invention

The example 4 represents an application of the improved dehydrochlorination reactive distillation, according to one aspect of the present invention. While the primary liquid feed is mixed with only 60% of the total caustic solution flowrate, the secondary feed joins separately another approximately 20% of the total caustic solution and after a vapor-liquid separation unit, enters two different trays located below the inlet of the liquid feed. The remaining part of the caustic is distributed in four different trays below the secondary feed liquid inlet.

Thanks to the energy contribute of the secondary feed the column operates at the same reflux ratio of example 1, but with a lower heat duty of the reboiler, as shown in the table 3

TABLE 3

| Example | Caustic excess % | Heat duty KW | Steam/ECH ratio Kg/Kg | Column reflux ratio Kg/Kg |
|---|---|---|---|---|
| 4 | 5 | 4650 | 1.21 | 1.4 |

The attached table 4 shows the most representative results of the example 4.

TABLE 4

| Example | ECH yield % | Glycerol at bottom wt % | Residue TOC mg/l |
|---|---|---|---|
| 4 | 99.1 | 0.14 | 602 |

The values in tables 3 and 4, compared with the tables 1 and 2, emphasizes the advantages obtained by the arrangement of the invention. The distribution of the caustic soda in different points of the reactive column permits a considerable decrease of the hydrolysis reaction and of the organic content of the aqueous residue, expressed as Total Organic Carbon (TOC), while the vapor feed separately from the liquid feed allows a substantial reduction of the column energy consumption, expressed as Kg of steam consumed at the reboiler per kilogram of produced epichlorohydrin.

The invention claimed is:

1. A process for the continuous production of epichlorohydrin from dichlorohydrins in presence of caustic soda, comprising:
   a. producing the dichlorohydrins by a continuous catalyzed process using glycerol and hydrogen chloride as feedstocks, producing 1,3 dichlorohydrin with a selectivity higher than 90%; and
   b. a reactive column for the reaction of dichlorohydrin to epichlorohydrin is provided by single or multiple feed injections of dichlorohydrins and by multiple feed injections of caustic soda wherein a first part of caustic soda joining the dichlorohydrins in 5 to 20% stoichiometric defect with respect to the dichlorohydrins, while
   c. a final part of the caustic solution to bring again an amount of the caustic solution in stoichiometric excess not higher than 10% with respect to the dichlorohydrin, is added in an intermediate section, not less than two trays below the dichlorohydrin feed, of the reactive column, operating under slight vacuum, where the epichlorohydrin produced by reaction has been stripped out by a countercurrent stream of steam.

2. A process of dehydrochlorination for the continuous production of epichlorohydrin by the reaction of dichlorohydrin at concentration higher than 95%, according to claim 1, wherein the process comprises:
   a. contacting all the concentrated dichlorohydrin stream with only said first part of the caustic soda solution, in a mixer;
   b. feeding the combined stream from the mixer to a reactive distillation column, including, below the feed point, no more than three trays of the segment or disc and doughnut without downcomers, intrinsically having low liquid residence time, followed by no more than three trays of valve or sieve, having an higher efficiency;
   c. feeding the final part of the caustic soda solution distributed in one to three different trays below the high efficiency trays, in order to keep about constant at the points of injection along the column a mass ratio between the caustic soda and the dichlorohydrin;
   d. using, in the above section with caustic injection, trays, of the segmental or disc and doughnut without downcomers intrinsically having a low liquid residence time;
   e. using in the bottom section of the column, where almost all dichlorohydrin is reacted, valve or sieve trays, having high efficiency;
   f. vaporizing part of the aqueous product from the column bottom in a bottom reboiler using steam as heating medium, without direct use of live steam injected at the column bottom;
   g. stripping the epichlorohydrin in the column as soon the epichlorohydrin is formed, condensing the mixture of epichlorohydrin, water and small amount of light by-products from the column overhead in a condenser using cooling water or air, separating the resulting two liquid phases and refluxing to the column top section the aqueous phase, containing epichlorohydrin with concentration equal or higher of epichlorohydrin's solubility in water at the condensing temperature.

3. The process of dehydrochlorination of claim 2, wherein the operating pressure has a range between 200 mbar absolute and 1.5 bar absolute.

4. The process of dehydrochlorination of claim 2, wherein the operating temperature of the column bottom has a range between 75° C. and 110° C.

5. The process of dehydrochlorination of claim 2, wherein the caustic soda solution is at a concentration between 10 to 30 wt %.

6. The process of claim 5, wherein the aqueous product from the bottom of the reactive column has a sodium chloride concentration of at least 18 wt %, or below sodium chloride's solubility limit in water at the temperature of the column.

7. The process of dehydrochlorination of claim 2 point a, wherein the amount of caustic soda joining the dichlorohydrin feed in a mixer is at least 80%, but not higher than 95% of the stoichiometric value to convert the dichlorohydrin to epichlorohydrin and to neutralize hydrogen chloride in the feed to sodium chloride.

8. The process of dehydrochlorination of claim 2, wherein the total amount of caustic soda sent to the mixer of point a plus the amount sent to the multiple feed injection of the column of point c is at least 101% but not more than 110% of the stoichiometric value to convert the dichlorohydrin to epichlorohydrin and to neutralize hydrogen chloride in the feed to sodium chloride.

9. A process of dehydrochlorination for the continuous production of epichlorohydrin in a reactive column wherein, besides a main liquid feed with concentration of dichlorohydrin higher than 95%, another secondary vapor feed is present, containing water at more than 50 wt %, hydrogen chloride, dichlorohydrin and monochlorohydrins, wherein the process comprises:
  a. contacting the concentrated dichlorohydrin stream with only said first part of the caustic soda solution, in a mixer;
  b. feeding the combined stream from the mixer to a reactive distillation column, including, below the feed point, no more than three trays, of the segment or disc and doughnut without downcomers intrinsically having low liquid residence time, followed by no more than three valve or sieve trays, having a higher efficiency;
  c. contacting the vapor feed containing water, hydrogen chloride, dichlorohydrins and monochlorohydrins with a second stream of diluted caustic soda, in an amount corresponding to the neutralization of the vapor feed's acid content, in a second mixer;
  d. separating the vapor and liquid phases from the second mixer and feeding them to two different trays of the reactive column;
  e. feeding the final part of the caustic soda solution distributed in two to four different trays below the secondary feed section, in order to keep about constant at the points of injection along the column a mass ratio between the caustic soda and the dichlorohydrin;
  f. using, in the above section with caustic injections, trays of the segment or disc and doughnut without downcomers intrinsically having low liquid residence time;
  g. using in the bottom section of the column, where almost all dichlorohydrin is reacted, valve or sieve trays, having higher efficiency, minimizing the content of chlorinated organic in the bottom aqueous product;
  h. vaporizing part of the aqueous product from the column bottom in a bottom reboiler using steam, without direct use of live steam injected at the column bottom;
  i. stripping the epichlorohydrin in the column as soon it is formed, condensing the mixture of epichlorohydrin, water and small amount of light by-products from the column overhead in a condenser using cooling water or air, separating the resulting two liquid phases and refluxing to the column top section the aqueous phase, containing epichlorohydrin with concentration equal or slightly higher of epichlorohydrin's solubility in water at the condensing temperature.

10. The process of dehydrochlorination of claim 9, wherein the operating pressure has a range between 200 mbar absolute and 1.5 bar absolute.

11. The process of dehydrochlorination of claim 9, wherein the operating temperature of the column bottom has a range between 75° C. and 110° C.

12. The process of dehydrochlorination of claim 9, wherein the caustic soda solution is at a concentration between 10 to 30 wt.

13. The process of claim 12, wherein the aqueous product from the bottom of the reactive column has a sodium chloride concentration of at least 18 wt %.

14. The process of dehydrochlorination of claim 9 point a, wherein the amount of caustic soda joining the dichlorohydrin feed in a mixer is at least 80%, but not higher than 95% of the stoichiometric value to convert the dichlorohydrin to epichlorohydrin and to neutralize the hydrogen chloride in the feed to sodium chloride.

15. The process of dehydrochlorination of claim 9 point c, wherein the amount of caustic soda joining the vapor feed in a second mixing device is at least 110%, of the stoichiometric value to neutralize to sodium chloride the hydrogen chloride contained in the vapor feed.

16. The process of claim 15, further comprising, after the mixer, a separation of the resulting vapor and liquid phases, which are fed to two different trays of the reactive dehydrochlorination column.

17. The process of dehydrochlorination of claim 9, wherein the total amount of caustic soda sent to the mixer of points "a" and "c" plus the amount sent to the multiple feed injection of the column of point "e" is at least 101% but not more than 110% of the stoichiometric value to convert the dichlorohydrin to epichlorohydrin and to neutralize, if any, the hydrogen chloride in the feeds to sodium chloride.

18. The process of dehydrochlorination of claim 2, wherein the mixer is a static mixer.

19. The process of dehydrochlorination of claim 2, wherein the operating pressure has a range between 400 mbar absolute and 400 mbar.

20. The process of dehydrochlorination of claim 2, wherein the operating temperature of the column bottom has a range between 85° C. and 99° C.

* * * * *